United States Patent [19]

Troyer

[11] Patent Number: 4,607,453

[45] Date of Patent: Aug. 26, 1986

[54] HYBRID CORN PLANTS WITH IMPROVED STANDABILITY

[75] Inventor: A. Forrest Troyer, DeKalb, Ill.

[73] Assignee: DeKalb-Pfizer Genetics, DeKalb, Ill.

[21] Appl. No.: 703,587

[22] Filed: Feb. 21, 1985

[51] Int. Cl.[4] ............................................. A01H 1/02
[52] U.S. Cl. ......................................................... 47/58
[58] Field of Search ......................................... 47/58, 1

[56] References Cited

U.S. PATENT DOCUMENTS 4,368,592  1/1983  Welch ...................................... 47/58

Primary Examiner—Robert E. Bagwill
Attorney, Agent, or Firm—Charles J. Knuth; Peter C. Richardson; James H. Monroe

[57] ABSTRACT

Novel F1 hybrid corn plants DK 672, novel seeds of the hybrid, seeds produced by cultivation of the hybrid, cells which upon growth and differentiation produce the novel hybrid and a method to produce the novel hybrid are disclosed.

5 Claims, No Drawings

HYBRID CORN PLANTS WITH IMPROVED STANDABILITY

BACKGROUND OF THE INVENTION

This invention relates generally to the production of maize commonly known in the United States as corn and more particularly concerns the development and production of inbred and hybrid maize with certain desired characteristics.

Commercial hybrid maize normally grows to a height of nine to ten feet with each plant having either one or two ears. The ear normally grows about one-third the way up the plant or about three feet from the ground. Consequently the maize plant, while providing a large ear has a substantial leaf and stalk structure and a considerable mechanical stability problem in that the heavy ear is about three feet from the ground with six feet of stalk and the tassels extending above that. In the past, efforts have been made to develop strong stalks and branching of secondary roots in maize to help alleviate this problem. While these efforts have improved the mechanical stability of maize considerably, heavy wind storms and rain can still wreak havoc in a field of maize.

Accordingly, one of the objects of this invention is to provide a method to improve the mechanical stability of the plant.

While great gains have been made in the use of hybrid maize in the productivity and yield per acre, over that of inbred maize, further substantial gains due to hybrid vigor are not anticipated. Consequently, efforts must be directed to drastically changing the characteristics of the commercial maize plant by genetic or environmental manipulation.

Hence one of the objects of this invention is to significantly increase the yield per acre of maize. For example, in the Apr. 17, 1974 edition of The Wall Street Journal, the article entitled "In Search of Superbean", it was pointed out that soybeans could not easily be hybridized and therefore fell far behind corn in productivity increase. During the period of 1950 to 1973, soybeans increased in productivity from 21.8 to 27.8 bushels per acre while corn increased from 38.4 to 91.4 bushels per acre.

Other advantageous characteristics can also be sought by the methods of plant breeding and genetic manipulation. For example, the ability of the plant to stay green later in the season is advantageous as is the low placement of the ears in comparison to the plant height. The present invention for the first time provides a novel corn hybrid with all of these advantages and other advantageous characteristics as well.

SUMMARY OF THE INVENTION

The present invention comprises novel F1 generation hybrid corn plants designated DK 672 and deposited under accession number ATCC 40229 at the American Type Culture Collection, 12301 Parklawn Drive, Rockville, Maryland 20852. This invention further comprises novel hybrid corn seed DK 672 and the novel seeds produced by the cultivation of novel hybrid DK 672 corn plant. Cells which upon growth and differentiation produce novel hybrid corn plants DK 672 also form a part of this invention.

Finally, a novel process to produce novel hybrid corn seed DK 672 is claimed. The process comprises the steps of:

(a) planting in pollinating proximity seeds of corn varieties B73Ht and HBA1;
(b) cultivating corn plants resulting from said planting until time of flowering;
(c) emasculating said flowers of said plants of variety B73Ht;
(d) allowing natural cross pollination to occur between said varieties; and
(e) harvesting seeds produced on said plants of variety B73Ht.

DETAILED DESCRIPTION OF THE INVENTION

As the female parent used to produce the novel corn hybrid plants and seeds of the present invention a public line, B73Ht, is employed. This line was developed by Iowa State University, Ames, Iowa, where it is available to the public. A proprietary line HBA1 developed by DeKalb-Pfizer Genetics was employed as the male parent. This line has been deposited with the American Type Culture Collection, 12301 Parklawn Drive, Rockville, Maryland 20852, receiving accession number ATCC 40225. This work was carried out in seed production fields in Maui, Hi.

The two parent varieties were planted in pollinating proximity to each other in alternating rows. They also can be planted in blocks or in any convenient planting pattern that allows for free transfer of pollen. The plants of both varieties were allowed to grow unmolested until time of flowering with one application of fertilizer being applied at the seedling stage. They can be thinned at about the 3-leaf stage if desired, and also can be treated with other agricultural chemicals as considered appropriate by the seed grower. At the time of flowering, the tassels were removed from all plants of the female parent variety, B73Ht. This was accomplished by hand but can be done by machine as desired. Both varieties were then allowed to continue to grow and natural cross-pollination occurred by the action of wind as is normal in grasses including corn. Of course only pollen from the male parent variety, HBA1, was available for pollination, the tassels, or pollen bearing flowering parts, having been removed from all plants of female variety B73Ht. In this regard, the fields where the hybrid seeds of this invention were produced were well isolated from other corn fields to prevent any accidental contamination with ambient pollen. Such isolation techniques are normal in the seed corn industry and are well known to those skilled in the art.

Both parent varieties of corn were allowed to continue to grow but the ears from the female parent variety, B73Ht, only were harvested to obtain the novel F1 hybrid corn seeds, DK 672, of the present invention. The male parent variety ears can be harvested, if desired, for normal corn use but they will not be useful as hybrid seed corn.

To obtain the novel F1 hybrid corn plants of the present invention the seeds thus produced were planted at the next proper growing season. All parts of such plants of hybrid DK 672 are claimed as a part of the present invention including roots, stems, leaves and all flowering parts including pollen grains. The cells of plants of hybrid DK 672 which can be grown in culture and differentiated or regenerated to form hybrid plants also constitute a part of this invention. For details of generation procedures see C. E. Green and C. A. Rhodes, "Plant Regeneration In Tissue Culture of Maize", 1982, *Maize for Biological Research*, ed. W. F.

Sheridan, Plant Molecular Biology Association, Charlottesville, Va. p. 367-372.

Furthermore, the seeds produced by F1 hybrid DK 672 plants on maturity also form a part of the present invention. The novel F1 hybrid corn seeds, DK 672, were planted and the resulting hybrid plants were grown to maturity, the ears being harvested mechanically by normal means. Various measurements were made on the hybrid plants and on the seeds they produced and these results are summarized in Table 1 below. The results are shown in comparison with identically obtained results on a DeKalb-Pfizer Genetics commercial variety, DK 656, which matures at a similar rate and is thus a fair subject for comparison.

TABLE 1

| Hybrid | Yield in Bushels | Moisture Points | Plant Height Inches | Ear Height Inches | Stay Green | Not Stalk Lodged | Yield Moisture |
|---|---|---|---|---|---|---|---|
| DK 672 | 133.1 | 22.4 | 98.8 | 48.3 | 131.6 | 106.1 | 104.8 |
| DK 656 | 135.4 | 21.8 * | 94.4 * | 50.9 * | 95.9 * | 102.5 * | 109.8 * |

*statistically significant at the 1% level

An examination of Table 1 reveals that novel hybrid DK 672 is equivalent in yield to the similar and commercially successful hybrid DK 656. The novel variety of this invention is superior in the important characteristics of plant height, ear height (although the plant is higher thus producing more ensilage, the ear is lower, leading to less stalk lodging), stay-green capacity and lack of stalk lodging. These advantages have come about in a most unexpected and surprising way from the cross between the above disclosed parent varieties.

In addition to the observations shown above in Table 1, the hybrid of this invention has the following characteristics.

Plant
    Height (to tassel tip)—253 cm
    Ear height (to base of top ear)—124 cm
    Tillers—few
    Ears per stalk—1
Leaf
    Angle from stalk—upright
    Sheath pubescence—very
    Number—20.2
    Anthocyanin in sheath—absent
Tassel
    Length—34.7 cm
    Branches—some
    Branch angle—intermediate
    Anther color—yellow
    50% Pollen shed (days)—69
    50% Pollen shed (degree days)—1,526
Ear
    Silk Color—yellow
    Husk bracts—short
    Length—18.1 cm
    Shape—semi-conical
    Diameter—5.1 cm
    Kernel rows—18.4 cm
    Shank length—14.8 cm
    Husk number—7.7
    Husk length—21.6 cm
    Husk width—14.5 cm
    Husk cover—6.7 cm
    Husk area—2400 $cm^2$
    Cob color—red
    Cob diameter—3.0 cm
    glume color—medium green
Kernel
    Type—dent
    Color
        A. cap—deep yellow
        B. sides—deep yellow
    Form—elongated
    No. per pound—1,386
Disease resistance
    Northern leaf blight, Race 1—resistant
    Northern leaf blight, Race 2—resistant
    Southern leaf blight, Race 0—resistant
    *Kabatiella zeae*—resistant
    *Helminthosporium carbonum,* Race 3—resistant This disclosure is illustrative and the present invention is defined in the appended claims.

I claim:

1. Novel F1 generation hybrid corn plants DK 672.
2. Novel F1 generation hybrid corn seed DK 672.
3. Seeds produced by the cultivation of the novel hybrid plants of claim 1.
4. Cells which upon growth and differention produce the novel hybrid corn plants of claim 1.
5. A method to produce novel hybrid corn seed DK 672 comprising the steps of:
    (a) planting in pollinating proximity seeds of corn varieties B73Ht and HBA1;
    (b) cultivating corn plants resulting from said planting until time of flowering;
    (c) at said flowering time, emasculating said flowers of said plants of variety B73Ht;
    (d) allowing natural cross pollination to occur between said varieties; and
    (e) harvesting seeds produced on said plants of variety B73Ht.

* * * * *